United States Patent
Li et al.

(10) Patent No.: US 12,150,766 B2
(45) Date of Patent: Nov. 26, 2024

(54) VISUAL PERCEPTION-BASED EMOTION RECOGNITION METHOD

(71) Applicant: Shenzhen Xiangsuling Intelligent Technology Co., Ltd., Shenzhen (CN)

(72) Inventors: Danjiang Li, Guiyang (CN); Ping Liu, Guiyang (CN); Ping Li, Guiyang (CN)

(73) Assignee: Shenzhen Xiangsuling Intelligent Technology Co., Ltd., Shenzhen (CN)

( * ) Notice: Subject to any disclaimer, the term of this patent is extended or adjusted under 35 U.S.C. 154(b) by 364 days.

(21) Appl. No.: 17/681,727

(22) Filed: Feb. 26, 2022

(65) Prior Publication Data
US 2022/0280087 A1 Sep. 8, 2022

(30) Foreign Application Priority Data
Mar. 2, 2021 (CN) .......................... 202110228631.9

(51) Int. Cl.
| | | |
|---|---|---|
| A61B 5/16 | (2006.01) | |
| A61B 5/00 | (2006.01) | |
| A61B 5/024 | (2006.01) | |
| G06N 3/084 | (2023.01) | |
| G06V 40/16 | (2022.01) | |

(52) U.S. Cl.
CPC .......... A61B 5/165 (2013.01); A61B 5/02405 (2013.01); A61B 5/7267 (2013.01); G06N 3/084 (2013.01); G06V 40/168 (2022.01); G06V 40/172 (2022.01)

(58) Field of Classification Search
None
See application file for complete search history.

(56) References Cited

U.S. PATENT DOCUMENTS

| | | | | |
|---|---|---|---|---|
| 2014/0316881 A1* | 10/2014 | Movellan | ........... | G06Q 30/0243 705/14.42 |
| 2016/0302711 A1* | 10/2016 | Frank | ..................... | A61B 5/746 |
| 2016/0321401 A1* | 11/2016 | Buil | ........................ | G16Z 99/00 |
| 2017/0311901 A1* | 11/2017 | Zhao | .................... | A61B 5/1102 |
| 2018/0314879 A1* | 11/2018 | Khwaja | ............. | A61B 5/02108 |

OTHER PUBLICATIONS

International Office Action (Publication No. 202110228631.9).

* cited by examiner

*Primary Examiner* — Leon Flores
(74) *Attorney, Agent, or Firm* — Forsgren Fisher McCalmont DeMarea Tysver LLP; James M. Urzedowski; Daniel A. Tysver

(57) ABSTRACT

The present disclosure relates to the field of emotion recognition technologies, and specifically, to a visual perception-based emotion recognition method. The method in the present disclosure includes the following steps: step 1: acquiring a face video by using a camera, performing face detection, and locating a region of interest (ROI); step 2: extracting color channel information of the ROI for factorization and dimension reduction; step 3: denoising and stabilizing signals and extracting physiological parameters including heart rate and breathing waveforms, and heart rate variability (HRV); step 4: extracting pre-training nonlinear features of the physiological parameters and performing modeling and regression of a twin network-based support vector machine (SVM) model; and step 5: reading a valence-arousal-dominance (VAD) model by using regressed three-dimensional information to obtain a specific emotional representation.

15 Claims, 6 Drawing Sheets

VISUAL PERCEPTION-BASED EMOTION RECOGNITION METHOD

CROSS REFERENCE TO RELATED APPLICATION(S)

This application claims priority to the Chinese Patent Application No. 202110228631.9, filed with the China National Intellectual Property Administration (CNIPA) on Mar. 2, 2021, and entitled "VISUAL PERCEPTION-BASED EMOTION RECOGNITION METHOD", which is incorporated herein by reference in its entirety.

TECHNICAL FIELD

The present disclosure relates to the field of emotion recognition technologies, and specifically, to a visual perception-based emotion recognition method.

BACKGROUND ART

Emotion recognition is a basis of effective information exchange between people. With the development and progress of computer technologies, visual emotion recognition has become an important field of artificial intelligence (AI) development, and can be widely used in all aspects of life, such as human-machine interaction, online learning, and interrogation assistance.

At present, vision-based emotion recognition technologies can be classified into the following two types: One type is based on facial expressions. Facial expressions are generally considered as physiological or psychological responses of people, used for emotional expression. Therefore, a facial microexpression-based technology generally uses a traditional machine learning or deep learning method to extract different expression features of face images, corresponding to basic expressions of a face expression library, namely, happiness, sadness, surprise, fear, anger, and disgust. In recent years, there are many studies focusing on emotion recognition of facial microexpressions. The other type is based on physiological signals of images or videos. Human physiological signal features are abstract representations of human emotions, with an extremely high correlation. With the in-depth study based on remote physiological signals, a reliable basis is provided for mappings from visual physiological signals to emotional representations. Generally, physiological signals such as a heart rate, breathing, and blood oxygen are directly extracted from face videos for analysis and classification to obtain several types of basic emotional expressions corresponding to categorical emotion models.

In fact, emotion changes are not all included in facial expression changes, and facial expressions can be autonomously controlled. Therefore, facial expression analysis-based emotion recognition is prone to misjudgment. In real scenes, people involuntarily move or there are specific light changes on faces. This makes physiological signals extracted from videos contaminated. Therefore, feature analysis and emotion association based on these signals are not rigorous. In addition, a general categorical emotion model cannot cover more emotional expressions, resulting in rough emotion classification.

In summary, emotion recognition based on facial expressions or physiological signals of images or videos in the prior art is prone to misjudgment, lacks rigor, and has narrow coverage of emotion expression analysis. Therefore, there is an urgent need for a visual perception-based emotion recognition method featuring more accurate and rigorous emotion recognition and wider coverage of emotion expression analysis.

SUMMARY

The present disclosure provides a visual perception-based emotion recognition method to resolve the problems that emotion recognition based on facial expressions or physiological signals of images or videos in the prior art is prone to misjudgment, lacks rigor, and has narrow coverage of emotion expression analysis. In the present disclosure, by combining a face video with a facial recognition algorithm and using physiological parameters including heart rate and breathing waveforms, and heart rate variability (HRV), reliable signal features are used for deep learning modeling after signal denoising and stabilization are performed, and on this basis, a valence-arousal-dominance (VAD) model is read to obtain a specific emotional representation. In this way, various emotion changes of a testee can be accurately analyzed. In addition, through this method, emotion recognition is not prone to misjudgment, and coverage of emotion expression analysis is wider.

To achieve the foregoing objective, the present disclosure adopts the following technical solutions:

A visual perception-based emotion recognition method includes the following steps:

step 1: acquiring a face video by using a camera, performing face detection, and locating a region of interest (ROI);

step 2: extracting color channel information of the ROI for factorization and dimension reduction;

step 3: denoising and stabilizing signals and extracting physiological parameters including heart rate and breathing waveforms, and HRV;

step 4: extracting pre-training nonlinear features of the physiological parameters and performing modeling and regression of a twin network-based support vector machine (SVM) model; and step 5: reading a VAD model by using regressed three-dimensional information to obtain a specific emotional representation.

Step 1 may specifically include: acquiring RGB video information containing a face region, process the video information by using face detection and feature point locating algorithms to obtain a position of a face and coordinate information of a feature point in an image, and selecting a rectangular region containing a cheek as the ROI based on the coordinate information of the feature point.

Further, step 2 may specifically include the following steps:

step 2.1: converting a color space of the ROI to a CIELab color space and a YUV color space; and step 2.2: equally dividing the ROI into n regions, obtaining averages of a, b, U, and V channels in a time window T, concatenating the averages to obtain a feature matrix $F_{n \times T}$ of the video, and performing non-negative matrix factorization on the feature matrix $F_{n \times T}$ by using the following formula:

$$F_{n \times T} \approx MN$$

where M and N represent two non-negative matrices, values of elements in the matrices are greater than 0, and n represents the number of regions in the ROI; and an error matrix E is expressed as $E = F_{n \times T} - MN$, it is assumed that the error matrix E conforms to a Gaussian distribution, the matrices M and N are obtained through multiplicative iteration, the two non-negative matrices M and N obtained through separation are multiplied to obtain a reconstruction matrix, and a maximum singular value of the reconstruction matrix is obtained, where the maximum singular value is a one-dimensional signal most related to a heart rate.

Further, step 3 may specifically include the following steps:

step 3.1: performing fast Fourier transform (FFT) on the one-dimensional signal to obtain a frequency-domain signal, filtering out noise out of a heart rate frequency band and a breathing frequency band to obtain a heart rate signal and a breathing signal with the out-of-band noise eliminated, eliminating in-band noise of the heart rate signal and the breathing signal through least squares smooth filtering, and enhancing and stabilizing the data through cubic spline interpolation to obtain a denoised remote heart rate waveform signal $OS_{HR}$ and breathing waveform signal $OS_{BR}$;

step 3.2: analyzing power spectral densities (PSDs) of $OS_{HR}$ and $OS_{BR}$, finding a frequency corresponding to a peak of each PSD, that is, obtaining a heart rate fundamental frequency and a breathing fundamental frequency, and multiplying the heart rate fundamental frequency and the breathing fundamental frequency by 60 to obtain the heart rate and a breathing value;

step 3.3: performing window sliding on the signal $OS_{HR}$ to determine a position of the peak, setting a heartbeat period window $\omega_b$ and a contraction peak period window $\omega_p$, performing FFT on the signal $OS_{HR}$, obtaining frequencies $f_{b[i]}$ and $f_{p[i]}$ at each time point i, and calculating $\omega_{b[i]}$ and $\omega_{p[i]}$ as follows: $\omega_{b[i]}=1/f_{b[i]}$ and $\omega_{p[i]}=1/f_{p[i]}$; and step 3.4: calculating thresholds $win_1$ and $win_2$ based on the heartbeat period window $\omega_b$ and the contraction peak period window $\omega_p$, respectively.

Further, the following formulas are used to calculate the thresholds $win_1$ and $win_2$ in step 3.4, respectively:

$$win_1 = \frac{1}{\omega_b}(OS_{HR}(i - \omega_b/2) + \ldots + OS_{HR}(i) + \ldots + OS_{HR}(i + \omega_b/2)$$

$$win_2 = |\omega_p|$$

where $OS_{HR}$ represents a remote heart rate waveform signal, $\omega_b$ represents the heartbeat period window, $\omega_p$ represents the contraction peak period window, i represents the time point, and $OS_{HR}(i)$ represents a remote heart rate waveform signal value at the time point i.

If $OS_{HR}(i)$ in the heartbeat period window is greater than $win_1$, a corresponding region is regarded as the ROI; if a width of the ROI is greater than $win_2$, it is considered that a peak detection condition is met; and a maximum value in the ROI is used as the peak, and the HRV is calculated based on a position difference between peaks.

Further, step 4 may specifically include the following steps:

step 4.1: extracting pre-training features of a pulse timing signal and a breathing timing signal, and a feature combination of the HRV; and step 4.2: performing network building and regression.

The extracting pre-training features of a pulse timing signal and a breathing timing signal in step 4.1 may specifically include the following steps:

step (1): extracting features of the remote heart rate waveform timing signal and a raw breathing waveform timing signal from a fixed-length time window through discrete wavelet transform, and obtaining detail coefficients of second, third, and fourth scales, an overview coefficient of the fourth scale, and an autocorrelation coefficient of the overview coefficient to form multidimensional feature sample points of each remote heart rate and breathing waveform timing signal sample; and step (2): using a Euclidean distance as a distance measure to calculate a discrete value to measure a distance between the feature sample points, where any several feature sample points constitute a feature combination, and each feature combination corresponds to a divergence value based on a pre-training distance measure, and normalizing the divergence value to a unified interval to form the pre-training features $f_v(v=0, 1, \ldots k)$ of the heart rate timing signal and breathing timing signal for use during classification, where $f_v$ represents a pre-training feature set, and v represents a dimension of final features.

That the feature combination of the HRV is extracted in step 4.1 may specifically include the following steps:

step 4.1.1: performing short-term nonlinear analysis on the HRV by extracting time interval features between each two peak waves, using a $j^{th}$ heartbeat period as an abscissa and a $(j+1)^{th}$ heartbeat period as an ordinate, and drawing an elliptical region in a two-dimensional plane, where semi-major and semi-short axes of the ellipse are respectively SD1 and SD2. and SD1 and SD2 are calculated by using the following formulas, respectively:

$$SD1 = \frac{STD(Y - X)}{\sqrt{2}}$$

$$SD2 = \frac{STD(Y + X)}{\sqrt{2}}$$

where X and Y respectively represent sets of X and Y coordinates contained in elements within the ellipse region, and STD represents an operation of obtaining a standard deviation;

step 4.1.2: obtaining a sequence of N time intervals, and using approximate entropy ApEn to measure irregularity of a feature change of the time interval sequence, where given a sequence $RR=[RR_1, RR_2, \ldots RR_N]$, phase space reconstruction of the sequence RR is $x_p=[RR[p], RR[p+1] \ldots RR[p+m-1]]$, $p \in [1, 2, \ldots N]$, m=2, RR represents the time interval sequence, RR[p] represents a $p^{th}$ time interval, m represents an embedded dimension, and $x_p$ represents the phase space reconstruction; a vector set $X[s]=[x_1, x_2, \ldots x_{N-m+1}]$, $s \in [1, N-m+1]$ whose element $x_p$ is constituted, where $x_1$ represents a sequence at a first moment; a distance $d[X[q], X[t]]$ between any two vectors $X[q]$ and $X[t]$ is defined as a difference between maximum absolute values of their respective components; given $r=0.2 \times SDNN$, where SDNN represents a standard deviation of the time interval sequence; and a number of $d[X[q], X[t]]<r$ is calculated for each vector, and then compared with a total number $N-m+1$ to obtain a probability $C_i^m(r)$, where the following formula is used:

$$C_i^m(r) = \frac{\text{number of } \{d[X[q], X[t]] \le r\}}{N - m - 1}, q, t \in [1, N - m + 1]$$

where number of represents an operation of counting a number;

step 4.1.3: calculating a follower index $\Phi^m(r)$ by obtaining a natural logarithm of each $C_i^m(r)$, a sum of the logarithms, and then an average of the logarithms by using the following formula:

$$\Phi^m(r) = \frac{1}{N-m+1} \sum_{i=1}^{N-m+1} \ln C_i^m(r);$$

where ln represents a logarithmic function, $\Sigma$ represents a summation function, and finally, approximate entropy ApEn of the time interval sequence is calculated by the following formula:

$$ApEn(m,r,N) = \Phi^m(r) - \Phi^{m+1}(r)$$

where m and N are natural numbers, $\Phi^m(r)$ represents an $m^{th}$ follower index, $\Phi^{m+1}(r)$ represents an $(m+1)^{th}$ follower index, and the extracted feature combination of the HRV is {SD1, SD2, ApEn(0.2)}.

The performing network building and regression in step 4.2 may specifically include: inputting a feature combination set $\{f_i, SD1, SD2, ApEn(0.2)\}$ into the twin network-based SVM model, and connecting a softmax layer, namely, a last layer of the twin network to the SVM model for multidimensional classification, where the SVM model finally outputs a nonlinear three-dimensional feature vector extracted from each time window of an HRV timing signal obtained from the heart rate and breathing signals; and the feature combination set is calibrated to a specific emotional state and then input to the network to form an end-to-end learning process that allows the neural network to model nonlinear dependence between a physiological signal in a user's resting state and a physiological signal during emotional arousal.

Further, that the VAD model is read by using the regressed three-dimensional information to obtain the specific emotional representation in step 5 may specifically include the following steps:

step 5.1: using a predefined VAD emotion dimension model, where the VAD emotion dimension model has a numerical distribution of 1,280 emotion points in three axes, and arousal, valence, and dominance are continuous values, with a value range of [0-9];

step 5.2: training two branch networks of the twin network-based SVM model, where current emotion feature data is input to one branch, and specified neutral emotion feature data is input to the other branch; and step 5.3: training the network through backpropagation of time and stochastic gradient descent to resolve three-valued regression problems related to the user's arousal, valence, and dominance levels, eventually corresponding to a specific emotional state of the VAD model.

The present disclosure has the following beneficial effects:

(1) In the present disclosure, by combining the face video with a facial recognition algorithm and using the physiological parameters including the heart rate and breathing waveforms, and HRV, reliable signal features are used for deep learning modeling after signal denoising and stabilization are performed, and on this basis, the VAD model is read to obtain the specific emotional representation. In this way, various emotion changes of a testee can be accurately analyzed. In addition, through this method, emotion recognition is not prone to misjudgment, and coverage of emotion expression analysis is wider.

(2) The method in the present disclosure is cost-effective, easy to operate, and very suitable for deployment to real-life scenarios.

BRIEF DESCRIPTION OF THE SEVERAL VIEWS OF THE DRAWINGS

The present disclosure will be further described below with reference to the accompanying drawings.

DETAILED DESCRIPTION OF THE EMBODIMENTS

To enable a person skilled in the art to better understand the present disclosure, the present disclosure is further described below in detail with reference to the accompanying drawings and the following embodiments.

Embodiment

Figure 1:
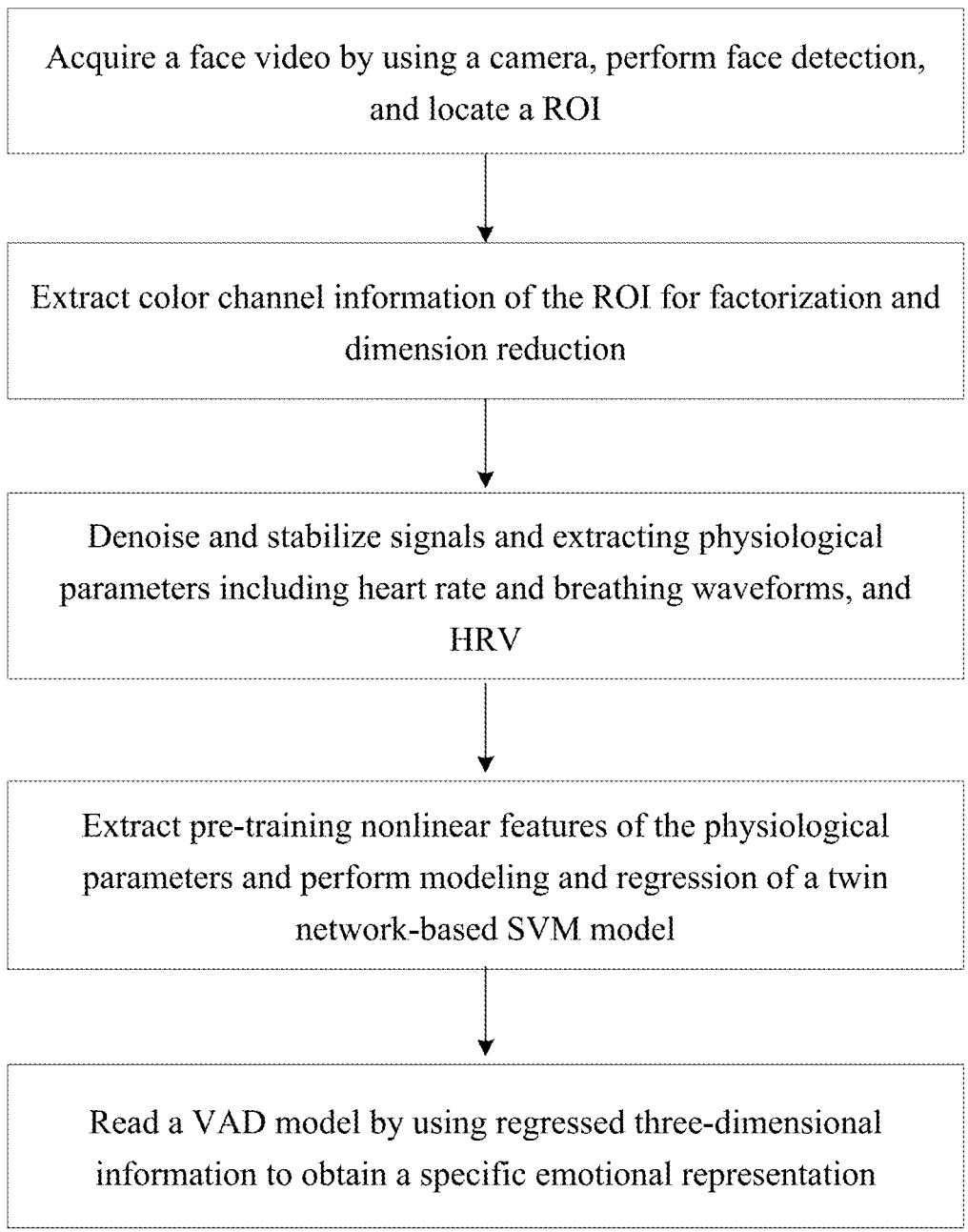
FIG. 1 is a flowchart according to the present disclosure.
Figure 2:
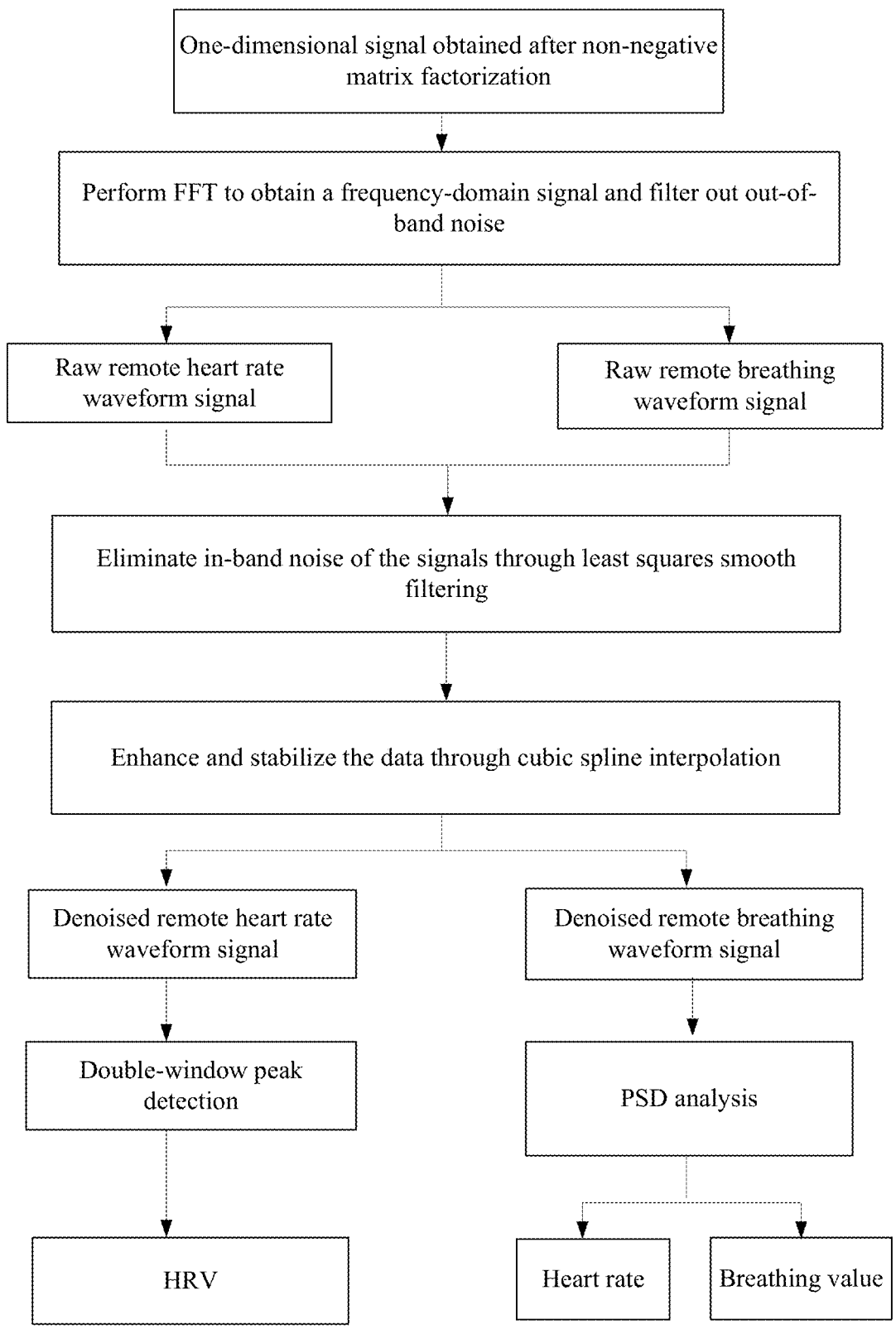
FIG. 2 is a flowchart of a method for denoising and stabilizing a heart rate waveform signal and a breathing waveform signal, and extracting physiological parameters according to the present disclosure.
Figure 3:
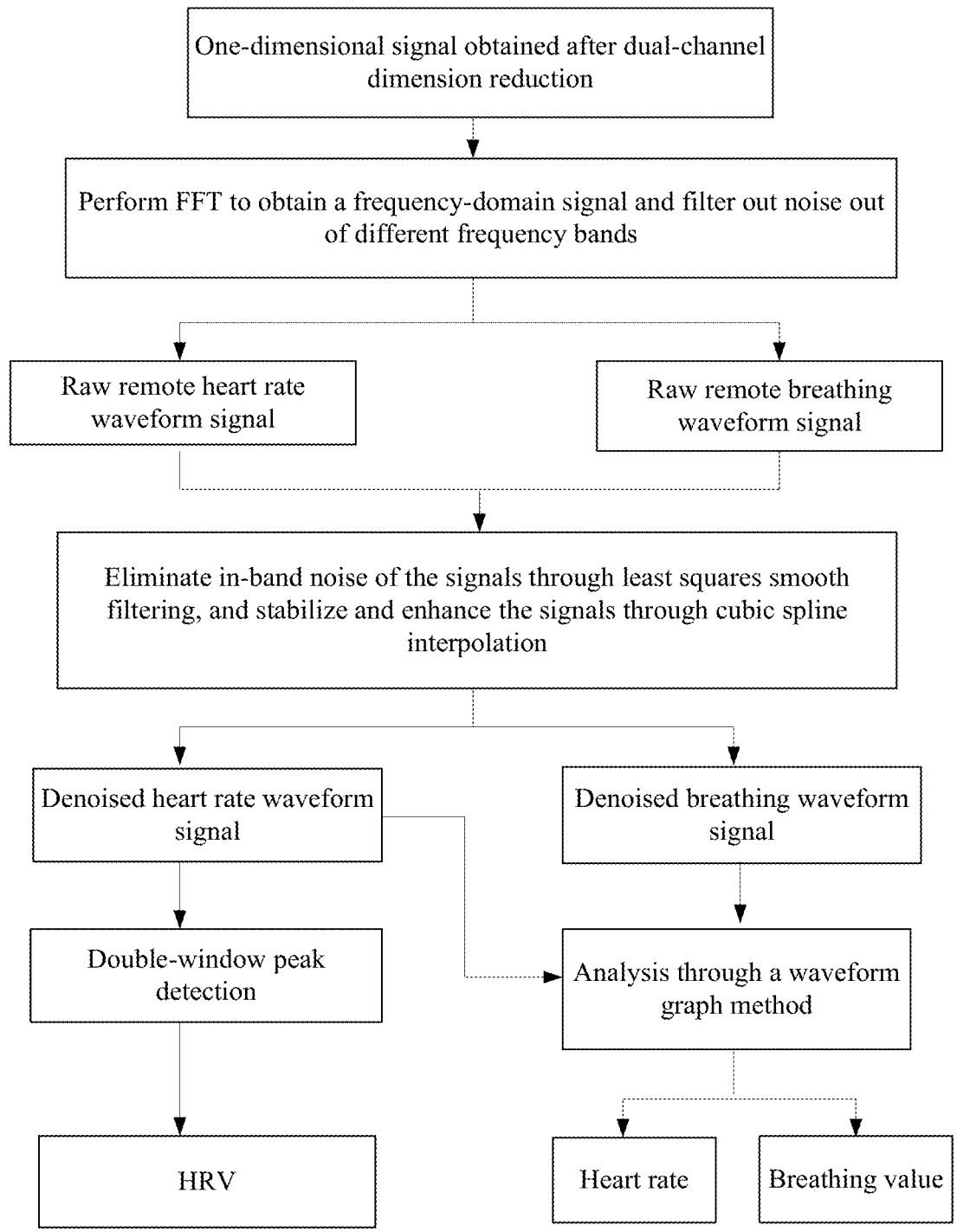
FIG. 3 is a flowchart of another method for denoising and stabilizing a heart rate waveform signal and a breathing waveform signal, and extracting physiological parameters according to the present disclosure.
Figure 4:
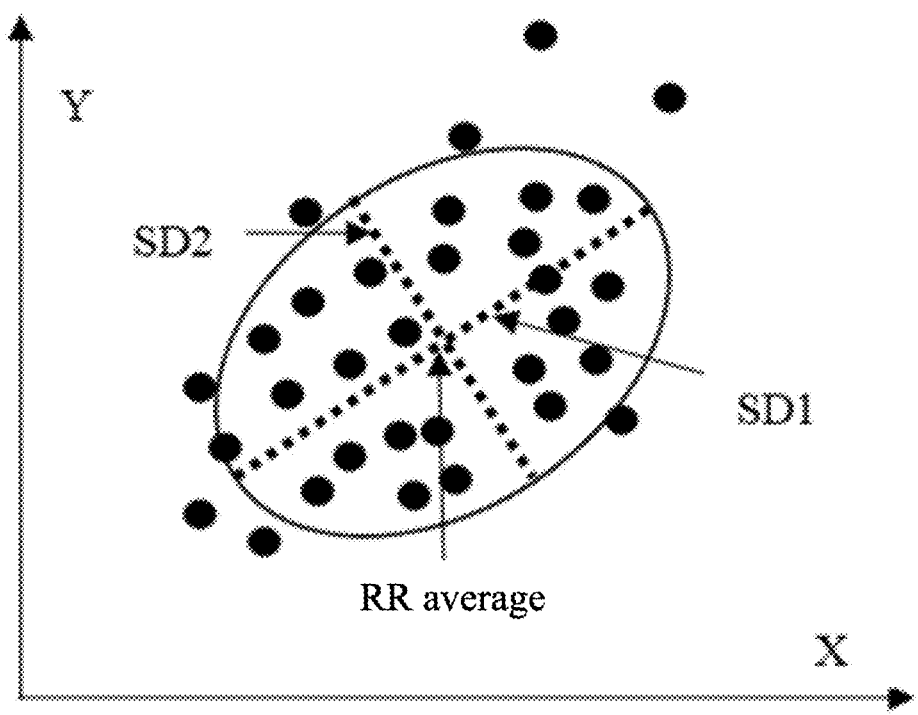
FIG. 4 is a diagram of performing short-term nonlinear analysis on HRV according to the present disclosure.
Figure 5:
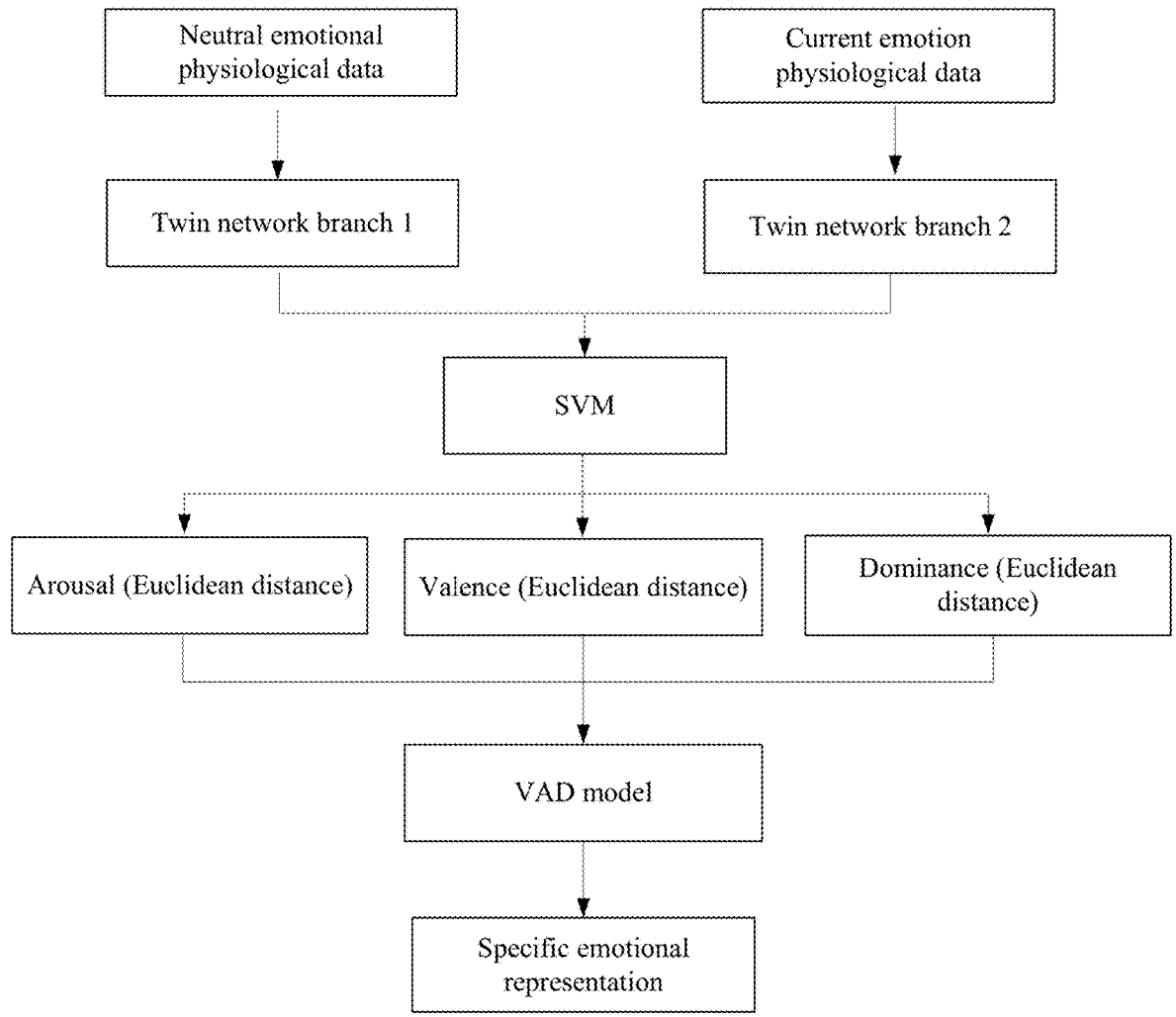
FIG. 5 is a basic flowchart of emotion prediction according to the present disclosure.
Figure 6:
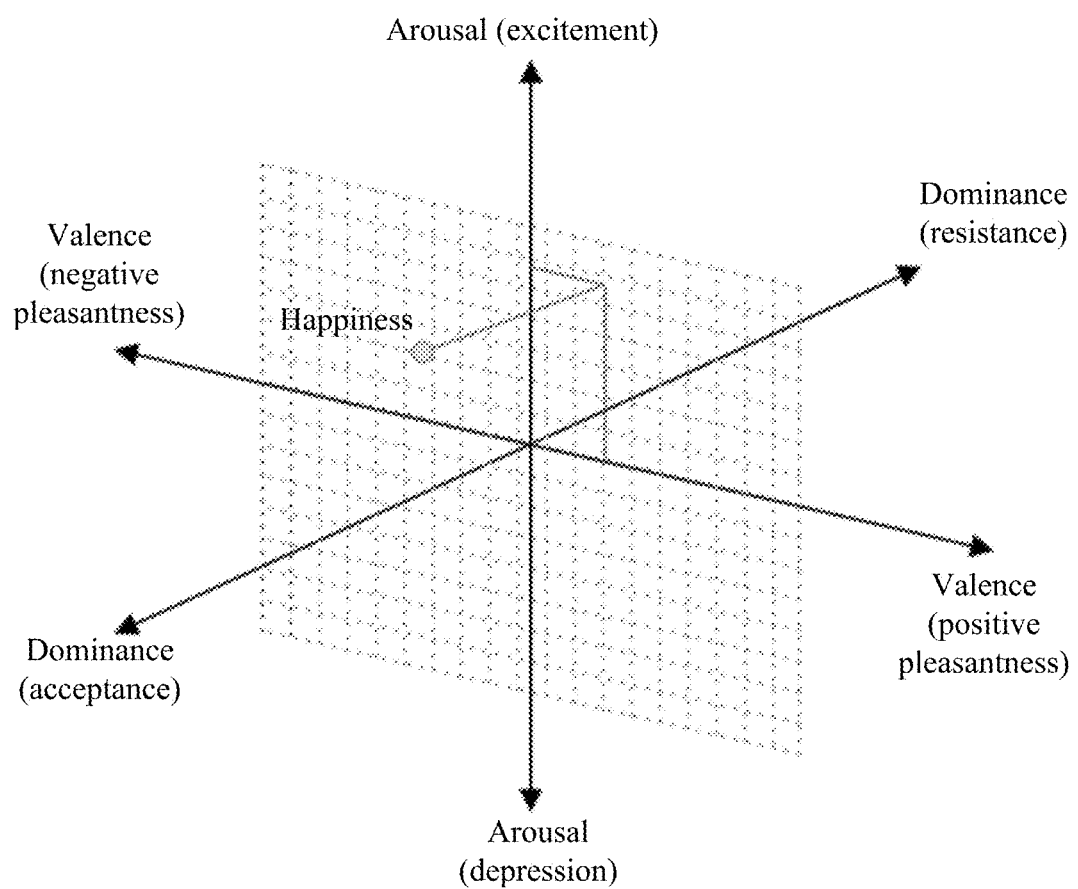
FIG. 6 is a diagram of a VAD model according to the present disclosure.

As shown in FIG. 1 to FIG. 6, a visual perception-based emotion recognition method is provided in this embodiment to resolve the problems that emotion recognition based on facial expressions or physiological signals of images or videos in the prior art is prone to misjudgment and has narrow coverage of emotion expression analysis. In addition, the recognition method is highly portable, cost-effective, and very suitable for deployment to real-life scenarios. The emotion recognition method includes the following steps:

Step 1: Acquire a face video by using a camera, perform face detection, and locate an ROI.

Step 1 may specifically include: Acquire RGB video information containing a face region by using a camera with a frame rate of 60 Hz, process the video information by using face detection and feature point locating algorithms to obtain a position of a face and coordinate information of a feature point in an image, and select a rectangular region containing a cheek as the ROI based on the coordinate information of the feature point.

In an optional implementation, step 1 may be as follows: Capture the face video by using the camera, compress and preprocess the face video, and perform face detection and ROI locating on a preprocessed video. Step 1 may specifically include the following steps:

Step 1.1: Acquire a visible light or near-infrared RGB video containing a face region based on a V4L2 framework to obtain the face video.

Specifically, at least 25 visible light or near-infrared 940-nm video frames are acquired per second based on the V4L2 framework to acquire the visible light or near-infrared RGB video containing the face region to obtain the face video, and the face video is used as an input source. In other words, the face video in this embodiment may be a visible light or near-infrared video.

Step 1.2: Compress and preprocess the face video to obtain the preprocessed video, where the preprocessing includes image distortion correction and exposure correction.

Specifically, each frame of the acquired face video is an NV12 image. The NV12 image is compressed into a YUV420 image, and preprocessing such as image distortion correction and exposure correction is performed on the YUV420 image to obtain the preprocessed video.

Step 1.3: Perform the face detection and ROI locating on the preprocessed video.

Specifically, step 1.3 may specifically include the following steps:

Step 1.3.1: Perform the face detection on the preprocessed video by using a NanoDet model to determine the face region.

More specifically, a target face is retrieved and tracked based on the NanoDet model in a 32-bit floating-point calculation unit and an 8-bit integer calculation unit to determine the face region. Because a posture of the face in front of the camera is arbitrary, different rotation angles may be presented. This poses a challenge to a direction and accuracy of the face detection. NanoDet is a lightweight multi-class object detection network. In this embodiment, angles of the face in a 2D plane are divided into eight parts, defined as eight classes, and input into NanoDet for retraining. Finally, a rotated face box and a corresponding angle are obtained to better perform face detection and determine the face region. Different from a general face detection method that is time-consuming and loses face angles, the face detection method in this embodiment uses the ultra-fast and lightweight NanoDet object detection model, changes a training strategy by replacing the number of original detected classes with different face angles for retraining, can quickly detect the face of different angles in the image, and is more in line with actual application scenarios.

Step 1.3.2: Train a region locating model based on an attention mechanism of deep learning, and perform ROI locating on the face region by using a trained region locating model to determine the ROI.

More specifically, a face box is a rectangular image containing a face. Part of the face box is an invalid region that attenuates signals and introduces noise. To extract a valid calculation region, in this embodiment, a face region image set is input into an attention network to generate a common valid region image mask set, so as to actively distinguish a pulsating region in the face box and obtain the ROI. Different from a method that uses the face region as the ROI and usually has problems of inaccurate locating and signal loss, the method in this embodiment uses the attention mechanism of deep learning to train a mask template set corresponding to most face pulsating regions, and can actively distinguish the valid signal region and the invalid region in the face region such that signal noise generated by motion and illumination is more robust.

Step 2: Extract color channel information of the ROI for factorization and dimension reduction.

Specifically, step 2 may specifically include the following steps:

Step 2.1: Because impact of human motion on intensity of the image is much greater than that on chrominance, convert a color space of the ROI to a CIELab color space and a YUV color space in this embodiment.

Step 2.2: Equally divide the ROI into n regions, obtain averages of a, b, U, and V channels in a time window T, concatenate the averages to obtain a feature matrix $F_{n \times T}$ of the video, and perform non-negative matrix factorization on the feature matrix $F_{n \times T}$ by using the following formula:

$$F_{n \times T} \approx MN$$

where M and N represent two non-negative matrices, values of elements in the matrices are greater than 0, and n represents the number of regions in the ROI.

A non-negative matrix factorization algorithm is used to find a minimum error between a product of the two non-negative matrices M and N and the feature matrix $E = F_{n \times T} - MN$. An error matrix E is expressed as $E = F_{n \times T} - MN$. It is assumed that the error matrix E conforms to a Gaussian distribution. The matrices M and N are obtained through multiplicative iteration. The two non-negative matrices M and N obtained through separation are multiplied to obtain a reconstruction matrix. A maximum singular value of the reconstruction matrix is obtained, where the maximum singular value is a one-dimensional signal most related to a heart rate.

In an optional implementation, in this embodiment, dual-channel dimension reduction may be performed on the image of the ROI and the signals are processed to obtain breathing and heart rate waveforms.

Specifically, in the visible light scenario, that is, when the face video is a visible light video, step 2 may include the following step: Obtain an 8-second image set of the ROI at a time in a form of a sliding window, and use a visible light dimension reduction formula to perform dimension reduction on RGB channel signals of the ROI of the visible light video to obtain a one-dimensional raw remote photoplethysmography (rPPG) signal raw(t).

The visible light dimension reduction formula is as follows:

$$raw(t) = C_1(t) + \alpha C_2(t)$$

where raw(t) represents the one-dimensional signal; $C_1(t)$ represents a first intermediate quantity; a represents a weight coefficient; and $C_2(t)$ represents a second intermediate quantity;

$$C_1(t) = G_n(t) - B_n(t)$$
$$C_2(t) = G_n(t) + B_n(t) - 2R_n(t)$$
$$\alpha = \frac{std(C_1(t))}{std(C_2(t))}$$

where $R_n(t)$, $G_n(t)$, and $B_n(t)$ represent the RGB channel signals obtained after the ROI of the visible light video is normalized in a time domain; and std represents an operation for obtaining a standard deviation.

In the infrared scenario, that is, when the face video is a near-infrared video, because the RGB channel signals have a same value in this case, the color space of the ROI of the near-infrared video is converted from the RGB color space to the CIELab color space. After the RGB channels are converted to LAB channels, because signal strength of an L channel is optimal, there is no need to perform dimension reduction, and a signal of the L channel is directly selected as the one-dimensional raw rPPG signal raw(t). Specifically, step 2 may specifically include the following steps:

(1) Convert a color space of the ROI of the near-infrared video from the RGB color space to the CIELab color space.

(2) Select an L channel signal of the ROI of the near-infrared video in the CIELab color space as a one-dimensional signal.

Different from a traditional dimensional reduction method for color spaces that is not suitable for infrared images, the dual-channel dimension reduction method is adopted in this embodiment, dimension reduction is performed on visible light using the RGB color space to obtain a one-dimensional signal, the L channel signal in the LAB color space is used in the infrared scenario, and luminance information of the image is more sensitive. After denoising, the waveform of the signal is closer to a raw signal waveform of the remote heart rate. This broadens application scenarios.

Step 3: Denoise and stabilize signals and extract physiological parameters including heart rate and breathing waveforms, and HRV.

Further, step 3 may specifically include the following steps:

Step 3.1: Perform FFT on the one-dimensional signal to obtain a frequency-domain signal, use a finite impulse response (FIR) filter (or a Butterworth filter) to filter out noise out of a heart rate frequency band and a breathing frequency band to obtain a heart rate signal and a breathing signal with the out-of-band noise eliminated, eliminate in-band noise of the heart rate signal and the breathing signal through least squares smooth filtering, and enhance and stabilize the data through cubic spline interpolation to obtain a denoised remote heart rate waveform signal $OS_{HR}$ and breathing waveform signal $OS_{BR}$. The smoothing does not change shapes and widths of the signals, and are performed to obtain pure color change signals of the face region.

step 3.2: analyzing power spectral densities (PSDs) of $OS_{HR}$ and $OS_{BR}$, finding a frequency corresponding to a peak of each PSD, that is, obtaining a heart rate fundamental frequency and a breathing fundamental frequency, and multiplying the heart rate fundamental frequency and the breathing fundamental frequency by 60 to obtain the heart rate and a breathing value;

In an optional implementation, a waveform graph method may alternatively be used to obtain heartbeat and breathing values in this embodiment. In this case, step 3.2 may alternatively be as follows: Convert $OS_{HR}$ and $OS_{BR}$ to binary visual images by using a trained waveform graph model, and performing model regression to obtain a heart rate corresponding to $OS_{HR}$ and a breathing value corresponding to $OS_{BR}$. T$_H$e trained waveform graph model is a regression network from a waveform graph to a heart rate, and a main network is a residual network (ResNet), which can convert waveform values to binary visual images and perform model regression. The heart rate can be obtained by inputting $OS_{HR}$ to the model, and the breathing value can be obtained by inputting $OS_{BR}$ to the model. The waveform graph method used in this embodiment has the following benefits: Different from a traditional Fourier spectrum analysis method that does not distinguish noise and a signal power peak, a method of converting image classification to numerical regression is adopted, a large number of real PPG waveform values are used to form a binary visual image, and simple network regression is performed by the ResNet to obtain the real heart rate. The waveform graph method can prevent a heart rate calculation error due to a false peak in the power spectrum, and is more flexible than spectrum analysis calculation.

Step 3.3: Perform window sliding on the signal $OS_{HR}$ to determine a position of the peak. Specifically, set two windows: a heartbeat period window $\omega_b$ and a contraction peak period window $\omega_p$. Average signal amplitude of a peak period is usually higher than that of the heartbeat period, and a contraction peak is usually a maximum value within the peak period. Therefore, perform FFT on the raw heart rate waveform signal $OS_{HR}$, obtain frequencies $f_{b[i]}$ and $f_{p[i]}$ at each time point i, and calculate $\omega_{b[i]}$ and $\omega_{p[i]}$ as follows: $\omega_{b[i]}/f_{b[i]}$ and $\omega_{p[i]}=1/f_{p[i]}$. For a stabilized remote pulse wave signal, a peak usually appears in a positive part, about half of the signal, and the peak period falls within the heartbeat period. Therefore, a size of the peak period window is set to 0.25 of the heartbeat period, and thus, the size of the other window is $\omega_p=0.25*\omega_b$.

Step 3.4: Calculate thresholds $win_1$ and $win_2$ based on the heartbeat period window $\omega_b$ and the contraction peak period window $\omega_p$, respectively.

Specifically, the following formulas are used to calculate the thresholds $win_1$ and $win_2$ in step 3.4, respectively:

$$win_1 = \frac{1}{\omega_b}(OS_{HR}(i-\omega_b/2) + \ldots + OS_{HR}(i) + \ldots + OS_{HR}(i+\omega_b/2))$$

$$win_2 = |\omega_p|$$

where $OS_{HR}$ represents a remote heart rate waveform signal, $\omega_b$ represents the heartbeat period window, $\omega_p$ represents the contraction peak period window, i represents the time point, and $OS_{HR}$ represents a remote heart rate waveform signal value at the time point i.

If $OS_{HR}(i)$ in the heartbeat period window is greater than $win_1$, a corresponding region is regarded as the ROI. If a width of the ROI is greater than $win_2$ it is considered that a peak detection condition is met. A maximum value in the ROI is used as the peak such that determining based on the two windows can reduce positioning errors of an interval between beats and a more accurate peak position can be obtained. The HRV is calculated based on a position difference between peaks.

In this embodiment, the window sliding is performed the signal $OS_{HR}$ to determine the position of the peak. A position difference sequence between the peaks is the HRV. The HRV is calculated through double-window peak detection.

Step 4: Extract pre-training nonlinear features of the physiological parameters and perform modeling and regression of a twin network-based SVM model.

Further, step 4 may specifically include the following steps:

Step 4.1: Randomly provide testees with video, image, and audio materials that can evoke various emotional states, and extract pre-training features of a heart rate timing signal and a breathing timing signal, and a feature combination of the HRV.

That the pre-training features of the heart rate timing signal and breathing timing signal are extracted in step 4.1 may specifically include the following steps:

Step (1): Use data acquired from a plurality of testees through the foregoing method and calibrated emotional states as a pre-training feature combination. Features of the remote heart rate waveform timing signal and raw breathing waveform timing signal are extracted from the time window through discrete wavelet transform. It is experimentally verified that feature frequency components that can best reflect a type difference in the remote heart rate waveform timing signal and the breathing waveform timing signal are concentrated on third and fourth scales of the wavelet transform. Discrete wavelet transform is performed on pre-processed raw heart rate waveform timing signal and breathing waveform timing signal samples. Detail coefficients of second, third, and fourth scales, an overview coefficient of the fourth scale, and an autocorrelation coefficient of the overview coefficient are obtained to form multidimensional feature sample points of each remote heart rate and breathing waveform timing signal sample.

Step (2): Use a Euclidean distance as a distance measure to calculate a discrete value to measure a distance between the feature sample points. Any several feature sample points constitute a feature combination. Each feature combination corresponds to a divergence value based on a pre-training distance measure. Normalize the divergence value to a unified interval to form the pre-training features $f_v (v=0, 1, \ldots k)$ of the heart rate timing signal and breathing timing signal for use during classification, where $f_v$ represents a pre-training feature set, and represents a dimension of final features.

That the feature combination of the HRV is extracted in step 4.1 may specifically include the following steps:

Step 4.1.1: Perform short-term nonlinear analysis on the HRV. Specifically, extract time interval features between each two peak waves. For a continuous heartbeat period, a $j^{th}$ heartbeat period is used as an abscissa, and a $(j+1)^{th}$ heartbeat period is used as an ordinate. Draw an elliptical region in a two-dimensional plane. A center of the ellipse is located at a coordinate point (x-axis heartbeat interval average, y-axis heartbeat interval average), and semi-major and semi-short axes of the ellipse are SD1 and SD2, respectively. SD1 and SD2 are calculated by using the following formulas, respectively:

$$SD1 = \frac{STD(Y - X)}{\sqrt{2}}$$

$$SD2 = \frac{STD(Y + X)}{\sqrt{2}}$$

where X and Y respectively represent sets of X and Y coordinates contained in elements within the ellipse region, and STD represents an operation of obtaining a standard deviation.

Step 4.1.2: Obtain a sequence of N time intervals, and use approximate entropy ApEn to measure irregularity of a feature change of the time interval sequence. Specifically, given a sequence $RR=[RR_1, RR_2, \ldots RR_N]$, phase space reconstruction of the sequence RR is $x_p=[RR[p], RR[p+1] \ldots, RR[p+m-1]]$, $p \in [1, 2, \ldots N]$, m=2, where RR represents the time interval sequence, RR[p] represents a $p^{th}$ time interval, m represents an embedded dimension, and $x_p$ represents the phase space reconstruction. A vector set $X[s]=[x_1, x_2, \ldots x_{N-m+1}]$, $s \in [1, N-m+1]$ whose element $x_p$ is constituted, where $x_1$ represents a sequence at a first moment. A distance $d[X[q], X[t]]$ between any two vectors $X[q]$ and $X[t]$ is defined as a difference between maximum absolute values of their respective components. Given $r=0.2 \times SDNN$, where SDNN represents a standard deviation of the time interval sequence. The number of $d[X[q], X[t]] < r$ is calculated for each vector, and then compared with the total number $N-m+1$ to obtain a probability $C_i^m(r)$. The following formula is used:

$$C_i^m(r) = \frac{\text{number of } \{d[X[q], X[t]] \leq r\}}{N - m - 1}, q, t \in [1, N - m + 1]$$

where number of represents an operation of counting a number.

Step 4.1.3: Calculate a follower index $\Phi^m(r)$ by obtaining a natural logarithm of each $C_i^m(r)$ a sum of the logarithms, and then an average of the logarithms by using the following formula:

$$\Phi^m(r) = \frac{1}{N - m + 1} \sum_{i=1}^{N-m+1} \ln C_i^m(r),$$

where ln represents a logarithmic function, and represents a summation function. Finally, approximate entropy ApEn of the time interval sequence is calculated by the following formula:

$$ApEn(m,r,N) = \Phi^m(r) - \Phi^{m+1}(r)$$

where m and N are natural numbers, $\Phi^m(r)$ represents an $m^{th}$ follower index, and $\Phi^{m+1}(r)$ represents an $(m+1)^{th}$ follower index. The extracted feature combination of the HRV is {SD1, SD2, ApEn(0.2)}.

Step 4.2: Perform network building and regression.

In step 4.2, the SVM model based on the twin neural network that shares parameters can resolve a problem that there are a large number of items to be classified, or a specific number cannot be determined, and is especially suitable for regression of any three-dimensional value. Therefore, the feature combination set $\{f_i, SD1, SD2, ApEn(0.2)\}$ is input into the twin network-based SVM model, and a softmax layer, namely, a last layer of the twin network is connected to the SVM model for multidimensional classification. The SVM model finally outputs a nonlinear three-dimensional feature vector obtained from each time window and extracted from a remote physiological signal. The feature combination set is calibrated to a specific emotional state and then input to the network to form an end-to-end learning process that allows the neural network to model nonlinear dependence between the physiological signal in the user's resting state and the physiological signal during emotional arousal.

Step 5: Read a VAD model by using regressed three-dimensional information to obtain a specific emotional representation.

Further, that the VAD model is read by using the regressed three-dimensional information to obtain the specific emotional representation in step 5 may specifically include the following steps:

Step 5.1: Use a predefined VAD emotion dimension model. The VAD emotion dimension model has a numerical distribution of 1,280 emotion points in three axes. Arousal, valence, and dominance are continuous values, with a value range of [0-9]. Any type of emotion (such as happiness) has different arousal, valence, and dominance values due to different stimulus effects. Because the three axes of this emotional model are continuous, all emotional state changes can be accepted.

Step 5.2: Train two branch networks of the twin network-based SVM model. Current emotion feature data is input to one branch, and specified neutral emotion feature data is input to the other branch.

Step 5.3: Train the network through backpropagation of time and stochastic gradient descent to resolve three-valued regression problems related to the user's arousal, valence, and dominance levels, eventually corresponding to the specific emotional state of the VAD model.

In general, psychological methods of studying emotions include a discrete method and a dimensional method. The discrete method indicates that emotions use a set of basic emotional states, which can be independently distinguished, such as anger, happiness, sadness, and love. The dimensional method concentrates emotional states in a smaller set of major dimensions, such as VAD. Most of influential methods for emotion mining in the past have basically focused on self-defining experimental discrete emotion models. Different emotional states such as degradation, embarrassment, and depression are considered as complex continuous emotional states. Discrete classification methods usually use expressions, actions, speech, multi-channel brain waves, and other multi-physiological metrics to establish correlation in a multi-modal way. However, a large number of experimental facts have proved that for different individuals and environments, a single label cannot be used to express complex emotional states. Therefore, the VAD emotion dimension model is used as a new classification standard, and is conducive to continuous and complex mixed emotional states of quantitative and qualitative analysis such that a plurality of emotional changes of the testees can be accurately analyzed, emotion recognition analysis through this method is not prone to misjudgment, and coverage of emotion expression analysis is wider.

The recognition method in this embodiment is a method for calculating a multidimensional emotional state of a testee based on a non-contact remote optical image. A physiological metric related to an emotional state and an optical signal of an effective region of human skin based on an RGB image or a grayscale image is first obtained. A deep learning model established based on the physiological metric maps several composite parameters of the emotion of the testee to quantify a qualitative emotional state. The foregoing technical solution can effectively resolve the problem of misjudgment of emotional recognition analysis, and has wider coverage of emotional expression analysis. The computing method in this embodiment can be implemented in a hardware processing unit of ARM a7, and local edge computing can be implemented by using neon, a 32-bit floating-point computing unit, and an 8-bit integer computing unit, without depending on a specific neural network to accelerate the computing unit and digital signal processing (DSP) unit. This has good support for universality of software transplantation. Hardware for implementing this method may be a single image sensor system on chip (SoC) apparatus based on a mature ARM 32-bit architecture or video cloud computing based on network compression transmission. This method features portability, lightweight, miniaturization, and real-time. Different from previous methods for emotion classification based on electrocardiogram (ECG or EKG) sensor metrics, this method can implement non-contact remote detection and computes features of emotion classification without relying on wearable sensors. Different from microexpression classification methods for a single facial feature, this method theoretically has the capability of calibration and prediction infinite types of complex emotional states. Different from millimeter waves (mmWaves), ultra-wideband (UWB), and other microwave pulsed coherent radar (PCR) physiological metric sensing methods, this method can identify objects and implement multi-person detection. Different from an existing commercial rPPG solution, this method has wide adaptability to daytime visible light conditions and night infrared conditions, and its implementation cost is much lower than existing ARM 64-bit or x86 platform solutions.

The foregoing embodiments are provided merely for an objective of describing the present disclosure and are not intended to limit the scope of the present disclosure. The scope of the present disclosure is defined by the appended claims. Various equivalent replacements and modifications made without departing from the spirit and scope of the present disclosure should all fall within the scope of the present disclosure.

What is claimed is:

1. A visual perception-based emotion recognition method, comprising the following steps: step 1: acquiring a face video by using a camera, performing face detection, and locating a region of interest (ROI); step 2: extracting color channel information of the ROI for factorization and dimension reduction to obtain a one-dimensional signal; step 3: denoising and stabilizing the one dimensional signal and extracting physiological parameters comprising heart rate and breathing waveforms, and heart rate variability (HRV); step 4: extracting pre-training nonlinear features of the physiological parameters and performing modeling and regression of a twin network-based support vector machine (SVM) model to obtain a nonlinear three-dimensional feature vector; and step 5: reading a valence-arousal-dominance (VAD) model by using regressed nonlinear three-dimensional feature vector to obtain a specific emotional representation; wherein reading the VAD model by using the regressed nonlinear three-dimensional feature vector to obtain the specific emotional representation in step 5 specifically comprises the following steps: step 5.1: training two branch networks of the twin network-based SVM model, wherein current emotion feature data is input to one branch, and specified neutral emotion feature data is input to the other branch; and step 5.2: training the twin network through backpropagation of time and stochastic gradient descent to resolve three-valued regression problems related to the user's arousal, valence, and dominance levels, eventually corresponding to a specific emotional state of the VAD model.

2. The visual perception-based emotion recognition method according to claim 1, wherein step 1 specifically comprises: acquiring RGB video information containing a face region, process the video information by using face detection and feature point locating algorithms to obtain a position of a face and coordinate information of a feature point in an image, and selecting a rectangular region containing a cheek as the ROI based on the coordinate information of the feature point.

3. The visual perception-based emotion recognition method according to claim 2, wherein step 2 specifically comprises the following steps:
    step 2.1: converting a color space of the ROI to a CIELab color space and a YUV color space; and
    step 2.2: equally dividing the ROI into n regions, obtaining averages of a, b, U, and V channels in a time window T, concatenating the averages to obtain a feature matrix $F_{n\times T}$ of the video, and performing non-negative matrix factorization on the feature matrix $F_{n\times T}$ by using the following formula:

$$F_{n\times T} \approx MN$$

wherein M and N represent two non-negative matrices, values of elements in the matrices are greater than 0, and n represents the number of regions in the ROI; and an error matrix E is expressed as $E=F_{n\times T}-MN$, it is assumed that the error matrix E conforms to a Gaussian distribution, the matrices M and N are obtained through multiplicative iteration, the two non-negative matrices M and N obtained through separation are multiplied to obtain a reconstruction matrix, and a maximum singular value of the reconstruction matrix is obtained, wherein the maximum singular value is a one-dimensional signal most related to a heart rate.

4. The visual perception-based emotion recognition method according to claim 3, wherein step 3 specifically comprises the following steps:

step 3.1: performing fast Fourier transform (FFT) on the one-dimensional signal to obtain a frequency-domain signal, filtering out noise out of a heart rate frequency band and a breathing frequency band to obtain a heart rate signal and a breathing signal with the out-of-band noise eliminated, eliminating in-band noise of the heart rate signal and the breathing signal through least squares smooth filtering, and enhancing and stabilizing the data through cubic spline interpolation to obtain a denoised remote heart rate waveform signal $OS_{HR}$ and breathing waveform signal $OS_{BR}$;

step 3.2: analyzing power spectral densities (PSDs) of $OS_{HR}$ and $OS_{BR}$, finding a frequency corresponding to a peak of each PSD, that is, obtaining a heart rate fundamental frequency and a breathing fundamental frequency, and multiplying the heart rate fundamental frequency and the breathing fundamental frequency by 60 to obtain the heart rate and a breathing value;

step 3.3: performing window sliding on the signal $OS_{HR}$ to determine a position of the peak, setting a heartbeat period window $\omega_b$ and a contraction peak period window $\omega_p$, performing FFT on the signal $OS_{HR}$, obtaining frequencies $f_{b[i]}$ and $f_{p[i]}$ at each time point i, and calculating $\omega_{b[i]}$ and $\omega_{p[i]}$ as follows: $\omega_{b[i]}=1/f_{b[i]}$ and $\omega_{p[i]}=1/f_{p[i]}$; and step 3.4: calculating thresholds $win_1$ and $win_2$ based on the heartbeat period window $\omega_b$ and the contraction peak period window $\omega_p$, respectively.

5. The visual perception-based emotion recognition method according to claim 3, wherein step 3 specifically comprises the following steps:

step 3.1: performing fast Fourier transform (FFT) on the one-dimensional signal to obtain a frequency-domain signal, filtering out noise out of a heart rate frequency band and a breathing frequency band to obtain a heart rate signal and a breathing signal with the out-of-band noise eliminated, eliminating in-band noise of the heart rate signal and the breathing signal through least squares smooth filtering, and enhancing and stabilizing the data through cubic spline interpolation to obtain a denoised remote heart rate waveform signal $OS_{HR}$ and breathing waveform signal $OS_{BR}$;

step 3.2: converting $OS_{HR}$ and $OS_{BR}$ into binary visual images by using a trained waveform graph model, and performing model regression to obtain a heart rate corresponding to $OS_{HR}$ and a breathing value corresponding to $OS_{BR}$;

step 3.3: performing window sliding on the signal $OS_{HR}$ to determine a position of the peak, setting a heartbeat period window $\omega_b$ and a contraction peak period window $\omega_p$, performing FFT on the signal $OS_{HR}$, obtaining frequencies $f_{b[i]}$ and $f_{p[i]}$ at each time point i, and calculating $\omega_{b[i]}$ and $\omega_{p[i]}$ as follows: $\omega_{b[i]}=1/f_{b[i]}$ and $\omega_{p[i]}=1/f_{p[i]}$; and step 3.4: calculating thresholds $win_1$ and $win_2$ based on the heartbeat period window $\omega_b$ and the contraction peak period window $\omega_p$, respectively.

6. The visual perception-based emotion recognition method according to claim 4, wherein the following formulas are used to calculate the thresholds $win_1$ and $win_2$ in step 3.4, respectively:

$$win_1 = \frac{1}{\omega_b}(OS_{HR}(i-\omega_b/2) + \ldots + OS_{HR}(i) + \ldots + OS_{HR}(i+\omega_b/2))$$

$$win_2 = |\omega_p|$$

wherein $OS_{HR}$ represents a remote heart rate waveform signal, $\omega_b$ represents the heartbeat period window, $\omega_p$ represents the contraction peak period window, i represents the time point, and $OS_{HR}(i)$ represents a remote heart rate waveform signal value at the time point i; and if $OS_{HR}(i)$ in the heartbeat period window is greater than $win_1$, a corresponding region is regarded as the ROI; if a width of the ROI is greater than $win_2$, it is considered that a peak detection condition is met; and a maximum value in the ROI is used as the peak, and the HRV is calculated based on a position difference between peaks.

7. The visual perception-based emotion recognition method according to claim 6, wherein step 4 specifically comprises the following steps:

step 4.1: extracting pre-training features of a pulse timing signal and a breathing timing signal, and a feature combination of the HRV; and step 4.2: performing network building and regression.

8. The visual perception-based emotion recognition method according to claim 7, wherein the extracting pre-training features of a remote heart rate waveform timing signal and a breathing timing signal in step 4.1 specifically comprises the following steps:

step (1): extracting features of the remote heart rate waveform timing signal and a raw breathing waveform timing signal from a fixed-length time window through discrete wavelet transform, and obtaining detail coefficients of second, third, and fourth scales, an overview coefficient of the fourth scale, and an autocorrelation coefficient of the overview coefficient to form multidimensional feature sample points of each remote heart rate and breathing waveform timing signal sample; and step (2): using a Euclidean distance as a distance measure to calculate a discrete value to measure a distance between the feature sample points, wherein any several feature sample points constitute a feature combination, and each feature combination corresponds to a divergence value based on a pre-training distance measure, and normalizing the divergence value to a unified interval to form the pre-training features $f_v$ (v=0, 1, . . . k) of the heart rate timing signal and breathing timing signal for use during classification, wherein $f_v$ represents a pre-training feature set, and v represents a dimension of final features.

9. The visual perception-based emotion recognition method according to claim 8, wherein the extracting a feature combination of the HRV in step 4.1 specifically comprises the following steps:

step 4.1.1: performing short-term nonlinear analysis on the HRV by extracting time interval features between each two peak waves, using a $j^{th}$ heartbeat period as an abscissa and a $(j+1)^{th}$ heartbeat period as an ordinate, and drawing an elliptical region in a two-dimensional plane, wherein semi-major and semi-short axes of the ellipse are respectively SD1 and SD2, and SD1 and SD2 are calculated by using the following formulas, respectively:

$$SD1 = \frac{STD(Y-X)}{\sqrt{2}}$$

$$SD2 = \frac{STD(Y+X)}{\sqrt{2}}$$

wherein X and Y respectively represent sets of X and Y coordinates contained in elements within the ellipse region, and STD represents an operation of obtaining a standard deviation;

step 4.1.2: obtaining a sequence of N time intervals, and using approximate entropy ApEn to measure irregularity of a feature change of the time interval sequence, wherein given a sequence RR=[$RR_1$, $RR_2$, ... $RR_N$], phase space reconstruction of the sequence RR is $x_p$=[RR[p], RR[p+1] ..., RR[p+m−1]], p∈[1, 2, ... N], m=2, RR represents the time interval sequence, RR[p] represents a $p^{th}$ time interval, m represents an embedded dimension, and $x_p$ represents the phase space reconstruction; a vector set X[s]=[$x_1$, $x_2$, ... $x_{N−m+1}$], s∈[1, N−m+1] whose element $x_p$ is constituted, wherein $x_1$ represents a sequence at a first moment; a distance d[X[q], X[t]] between any two vectors X[q] and X[t] is defined as a difference between maximum absolute values of their respective components; given r=0.2×SDNN, wherein SDNN represents a standard deviation of the time interval sequence; and a number of d[X[q], X[t]]<r is calculated for each vector, and then compared with a total number N−m+1 to obtain a probability $C_i^m(r)$, wherein the following formula is used:

$$C_i^m(r) = \frac{\text{number of } \{d[X[q], X[t]] \le r\}}{N-m-1}, q, t \in [1, N-m+1]$$

wherein number of represents an operation of counting a number;

step 4.1.3: calculating a follower index $\Phi^m(r)$ by obtaining a natural logarithm, of each $C_i^m(r)$, a sum of the logarithms, and then an average of the logarithms by using the following formula:

$$\Phi^m(r) = \frac{1}{N-m+1} \sum_{i=1}^{N-m+l} \ln C_i^m(r);$$

wherein ln represents a logarithmic function, Σ represents a summation function, and finally, approximate entropy ApEn of the time interval sequence is calculated by the following formula:

$$\text{ApEn}(m,r,N) = \Phi^m(r) - \Phi^{m+1}(r)$$

wherein m and N are natural numbers, $\Phi^m(r)$ represents an $m^{th}$ follower index, $\Phi^{m+1}(r)$ represents an $(m+1)^{th}$ follower index, and the extracted feature combination of the HRV is {SD1, SD2, ApEn(0.2)}.

10. The visual perception-based emotion recognition method according to claim 9, wherein the performing network building and regression in step 4.2 comprises: inputting a feature combination set {$f_i$, SD1, SD2, ApEn(0.2)} into the twin network-based SVM model, and connecting a softmax layer, namely, a last layer of the twin network to the SVM model for multidimensional classification, wherein the SVM model finally outputs a nonlinear three-dimensional feature vector extracted from each time window of an HRV timing signal obtained from the heart rate and breathing signals; and the feature combination set is calibrated to a specific emotional state and then input to the network to form an end-to-end learning process that allows the neural network to model nonlinear dependence between a physiological signal in a user's resting state and a physiological signal during emotional arousal.

11. The visual perception-based emotion recognition method according to claim 1, wherein step 1 specifically comprises the following steps:

step 1.1: acquiring a visible light or near-infrared RGB video containing a face region based on a V4L2 framework to obtain the face video;

step 1.2: compressing and preprocessing the face video to obtain a preprocessed video, wherein the preprocessing comprises image distortion correction and exposure correction; and step 1.3: performing the face detection on the preprocessed video and locating the ROI.

12. The visual perception-based emotion recognition method according to claim 11, wherein step 1.3 specifically comprises the following steps:

step 1.3.1: performing the face detection on the preprocessed video by using a NanoDet model to determine the face region; and step 1.3.2: training a region locating model based on an attention mechanism of deep learning, and performing ROI locating on the face region by using a trained region locating model to determine the ROI.

13. The visual perception-based emotion recognition method according to claim 12, wherein when the face video is a visible light video, step 2 specifically comprises the following step:

performing dimension reduction on RGB channel signals of the ROI of the visible light video by using a visible light dimension reduction formula to obtain a one-dimensional signal; wherein the visible light dimension reduction formula is as follows:

$$\text{raw}(t) = C_1(t) + \alpha C_2(t)$$

wherein raw(t) represents the one-dimensional signal; $C_1(t)$, represents a first intermediate quantity; α represents a weight coefficient; and $C_2(t)$ represents a second intermediate quantity;

$$C_1(t) = G_n(t) - B_n(t)$$

$$C_2(t) = G_n(t) + B_n(t) - 2R_n(t)$$

$$\alpha = \frac{std(C_1(t))}{std(C_2(t))}$$

wherein $R_n(t)$, $G_n(t)$, and $B_n(t)$ represent the RGB channel signals of the ROI of the visible light video.

14. The visual perception-based emotion recognition method according to claim 12, wherein when the face video is a near-infrared video, step 2 specifically comprises the following steps:
   converting a color space of the ROI of the near-infrared video from a RGB color space to a CIELab color space; and
   selecting an L channel signal of the ROI of the near-infrared video in the CIELab color space as a one-dimensional signal.

15. The visual perception-based emotion recognition method according to claim 1, wherein the reading the VAD model by using the regressed nonlinear three-dimensional feature vector to obtain the specific emotional representation in step 5 further specifically comprises the step of following steps: step 5.3: using a predefined VAD emotion dimension model, wherein the predefined VAD emotion dimension model has a numerical distribution of 1,280 emotion points in three axes, and arousal, valence, and dominance are continuous values, with a value range of [0-9].

* * * * *